United States Patent
Takuma et al.

Patent Number: 5,962,723
Date of Patent: Oct. 5, 1999

[54] METHOD FOR PRODUCING BENZYL BROMIDE DERIVATIVES

[75] Inventors: Kenzi Takuma, Kashiba; Akiko Kakimizu, Nishinomiya; Tomoyuki Kusaba, Takarazuka, all of Japan

[73] Assignee: Sumitomo Chemical Company, Limited, Osaka, Japan

[21] Appl. No.: 09/154,631

[22] Filed: Sep. 17, 1998

[30] Foreign Application Priority Data

Oct. 8, 1997 [JP] Japan ..................... 9-275733
Oct. 24, 1997 [JP] Japan ..................... 9-292316

[51] Int. Cl.⁶ ................................. C07C 229/28
[52] U.S. Cl. ........................................... 560/35
[58] Field of Search ............................. 560/35

[56] References Cited

U.S. PATENT DOCUMENTS

| | | | |
|---|---|---|---|
| 4,999,042 | 3/1991 | Anthony et al. | 71/88 |
| 5,047,408 | 9/1991 | Schuetz et al. | |
| 5,089,528 | 2/1992 | Wingert et al. | 514/640 |
| 5,145,980 | 9/1992 | Wenderoth et al. | 560/35 |
| 5,157,144 | 10/1992 | Anthony et al. | 560/35 |
| 5,185,342 | 2/1993 | Hayase et al. | |
| 5,510,344 | 4/1996 | Cliff et al. | |
| 5,563,159 | 10/1996 | Kusaba et al. | |
| 5,756,811 | 5/1998 | Assercq et al. | 560/35 |

FOREIGN PATENT DOCUMENTS

| | | |
|---|---|---|
| 20254426 | 1/1988 | European Pat. Off. |
| 5-294948 | 11/1993 | Japan |

*Primary Examiner*—Gary Geist
*Assistant Examiner*—Brian J. Davis
*Attorney, Agent, or Firm*—Birch, Stewart, Kolasch & Birch, LLP

[57] ABSTRACT

The method for producing the benzyl bromide derivatives of the formula:

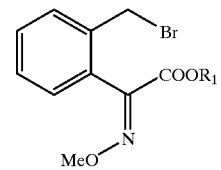

wherein $R_1$ represents a $C_1$ to $C_5$ alkyl group, which comprises reacting a 2-methylphenylacetic acid derivative of the formula:

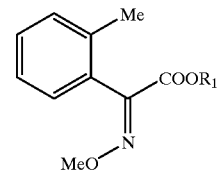

wherein $R_1$ represents the same meaning above, with bromine in the presence of an alkali metal salt. In case that $R^1$ is an ethyl or isopropyl group, the recrystallization of the above reaction product from aliphatic hydrocarbon solution gives the benzyl bromide derivatives efficiently and in high purity.

6 Claims, No Drawings

METHOD FOR PRODUCING BENZYL BROMIDE DERIVATIVES

FIELD OF THE INVENTION

The present invention relates to a method for producing benzyl bromide derivatives.

BACKGROUND ART

It is described that the dithiocarbonimide compounds shown by the formula (I):

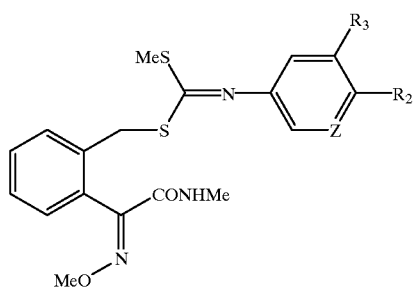

(wherein $R_2$ and $R_3$ are the same or different, and represent a hydrogen atom, $C_1$ to $C_6$ alkyl group, halogen atom, $C_1$ to $C_6$ alkoxy group, $C_1$ to $C_6$ haloalkyl group, $C_1$ to $C_6$ haloalkoxy group, or $R_2$ and $R_3$ form a methylenedioxy group optionally substituted by fluorine atom(s) together. Z represents a CH group or nitrogen atom) have an excellent plant disease controlling activity in U.S. Pat. No. 5,563,159. The said Patent specification shows the method for producing the said dithiocarbonimide compounds by using the benzyl bromide derivative of the formula (II):

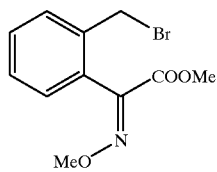

as an intermediate.

EP-254,426-A and EP-398,692-A show the method for producing benzyl bromide derivative of the formula (II) by reacting 2-methylphenylacetic acid derivative of the formula (III):

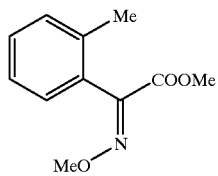

with N-bromosuccinimide(NBS). Furthermore, U.S. Pat. No. 5,047,408 shows the method for producing the benzyl bromide derivative of the formula (II) by reacting 2-methylphenylacetic acid derivative of the formula (III) with bromine under mercury lamp irradiation. However, the bromination process using NBS is not practical in industry and the reaction of bromine under mercury lump irradiation needs a photo-reaction facility. Therefore, it is desired to develop a method for producing the benzyl bromide derivative of the formula (II) that is advantageous in industry.

SUMMARY OF THE INVENTION

The present inventors intensely studied a method for producing the benzyl bromide derivatives of the formula (II) under the above circumstances. As a result, the present inventors found that the presence of an alkali metal salt helps to efficiently obtain a benzyl bromide derivative of the formula (IV) in the reaction of a 2-methylphenylacetic acid derivative, shown below in formula (V), with bromine, and completed the present invention.

Namely, the present invention provides a method for producing benzyl bromide derivatives of the formula (IV):

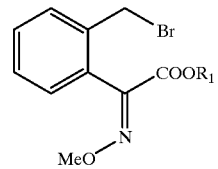

(wherein $R_1$ represents a $C_1$ to $C_5$ alkyl group), which comprises reacting 2-methylphenylacetic acid derivatives of the formula (V):

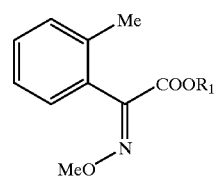

(wherein $R_1$ represents the same meaning above), with bromine in the presence of an alkali metal salt.

Furthermore, it was also found that the recrystallization of the reaction product from aliphatic hydrocarbon solution gives a benzyl bromide derivatives of the formula (IV) efficiently and in high purity in case that $R_1$ represents an ethyl or isopropyl group.

DETAILED DESCRIPTION

The present invention will be explained in detail below.

The alkali metal salt used in the present invention is exemplified by, for example, carbonates such as sodium carbonate, magnesium carbonate, potassium carbonate, calcium carbonate, sodium hydrogencarbonate, potassium hydrogencarbonate, and so on; phosphates such as sodium phosphate, potassium phosphate, and so on; carboxylates such as sodium acetate, potassium acetate, and so on. Sodium salts are preferably used.

The reaction is usually carried out in an inert solvent and the solvent is exemplified by halogenated aromatic hydrocarbon such as chlorobenzene, dichlorobenzene etc.; and halogenated aliphatic hydrocarbon such as chloroform, dichloroethane, etc.

The reaction temperature is usually within a range of 50 to 110° C., preferably 75 to 100° C., more preferably 80 to 95° C. The reaction time is usually within a range of 0.5 to 10 hours.

With regard to the amount of the reagents used in the reaction, the amount of the alkali metal salt is 1.5 to 5.0 mole and the amount of bromine is 0.7 to 1.5 mole, preferably 0.9 to 1.2 mole to one mole of the 2-methylphenylacetic acid derivative of the formula (V). However, in case of recovering and recycling the 2-methylphenylacetic acid derivative of the formula (V), the amount of bromine is desired to be 0.4 to 0.8 mole to one mole of the 2-methylphenylacetic acid derivative of the formula (V).

Bromine may be used as it is or as dilution with solvent. It is preferable to carry out the reaction using bromine vaporized by heating.

Alkali metal salt may be used as it is in the market, but it is preferable to use it soon after pulverizing.

Addition of a radical initiator is preferable though the reaction can proceed without it. The radical initiators are exemplified by benzoyl peroxide, 2,2'-azobisisobutyronitrile, 1,1'-azobis(1-cyclohexanenitrile), and so on. The amount of the radical initiator used for the reaction is 0.005 to 0.2 mole, preferably 0.01 to 0.1 mole to one mole of the 2-methylphenylacetic acid derivative of the formula (V).

After the reaction is completed, the alkali metal salt is usually filtered off, the organic layer is washed with water or diluted hydrochloric acid and concentrated to give the objective product.

In case that $R^1$ is an ethyl or isopropyl group, the product obtained above can be easily purified by the recrystallization from aliphatic hydrocarbons. The "aliphatic hydrocarbon" used for recrystallization in the present invention means non-aromatic hydrocarbon and it also contains alicyclic hydrocarbon. The aliphatic hydrocarbon is usually $C_{5-12}$ hydrocarbon and exemplified by n-hexane, n-heptane, n-octane, cyclohexane, cyclooctane, petroleum ether and the mixture therof. In particular, n-hexane, n-heptane, n-octane or the mixture therof is preferably used.

The used amount of the aliphatic hydrocarbons is usually 1 to 20 g, preferably 4 to 6 g per 1 g of the 2-methylphenylacetic acid derivative of the formula (V) used in the reaction as a starting material.

The recrystallization process comprises adding solvent to the crude product, heating the mixture, cooling it and filtering off. The heating temperature is usually in the range of 40° C. to the boiling point of the used solvent, preferably 50° C. to 90° C. The cooling for recrystallization is usually carried out in the range of −20° C. to 20° C., preferably −5° C. to 10° C. The cooling rate depends on the production scale and the other elements, but is usually 0.01 to 1.0° C./min, preferably 0.1 to 0.6° C./min.

The 2-methylphenylacetic acid derivatives of the formula (V) can be produced for example, according to the scheme below:

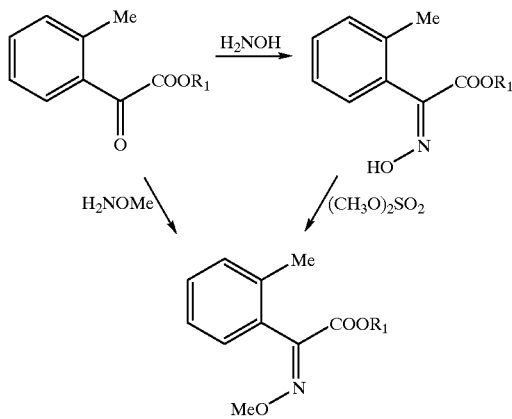

wherein $R_1$ means the same as above.

In the scheme, the 2-methylbenzoylformic acid esters can be prepared, for example, by the method shown in Tetrahedron Letters Vol.21, page 3539 (1980), Synthetic Communication Vol.11, page 943 (1981), etc.

EXAMPLES

Hereinafter, the present invention is explained more definitely in production examples but is not limited to these examples.

Production Example 1

A mixture of 6.36 g of sodium carbonate pulverized by a centrifugal pulverizer (60 mmol), 5.53 g of ethyl (E)-α-methoxyimino-o-tolylacetate (25 mmol) and 14.97 g of chlorobenzene was heated up to 85° C. with vigorous stirring. To the mixture, 6.00 g of a chlorobenzene solution containing 0.61 g of 1,1'-azobis(1-cyclohexanecarbonitrile) and 2.00 g of a chlorobenzene solution containing 4.80 g of bromine (30 mmol) were added dropwise at the same time over 1 hour. After the addition, the reaction mixture was kept at 86 to 88° C. for 2 hours, and then cooled to room temperature. After adding 50 ml of water to the reaction mixture, the organic layer was recovered, washed with 25 ml of water twice and the solvent was distilled off under reduced pressure to give 6.77 g of crude product. The crude product proved to contain 75.4% of the objective ethyl (E)-α-methoxyimino-2-(bromomethyl)phenylacetate, 4.5% of the starting material and 13.7% of ethyl (E)-α-methoxyimino-2-(dibromomethyl)phenylacetate (hereinafter, "Et-dibromo compound") by gas chromatography analysis. (% means areametric percentage.)

To 6.04 g of the crude product, 25.00 g of n-hexane was added and the mixture was heated to 73–75° C. to form a homogeneous solution. The solution was cooled to 3 to 5° C. over 3.5 hours and kept at the same temperature for one hour to age precipitated crystals. The crystals were filtered off in vacuo, washed with 12.00 g of cool n-hexane twice and dried to give 3.87 g of ethyl (E)-α-methoxyimino-2-(bromomethyl)phenylacetate. This purified product proved to contain 95.8% of the objective product, 0.6% of the starting material and 2.3% of Et-dibromo compound by gas chromatography analysis. mp 80.0–81.0° C.

$^1$H-NMR(CDCl$_3$/TMS,300 MHz, δ (ppm)) 1.33(3H,t,J=7 Hz), 4.05(3H,s), 4.34(2H,s), 4.35(2H,q,J=7 Hz), 7.15(1H, dd,J=8,1 Hz), 7.20–7.40(3H,m)

Production Example 2

A mixture of 6.36 g of sodium carbonate pulverized by a centrifugal pulverizer (60 mmol), 5.88 g of isopropyl (E)-α-methoxyimino-o-tolylacetate (25 mmol) and 14.97 g of chlorobenzene was heated up to 85° C. with vigorous stirring. Under a nitrogen stream, 4.80 g of vaporized bromine gas (30 mmol) was blown into the mixture over 1 hour while 6.00 g of a chlorobenzene solution containing 0.61 g of 1,1'-azobis(1-cyclohexanecarbonitrile) is added dropwise to the mixture at 90 to 100° C. After the blowing, the reaction solution was kept at 86 to 88° C. for 2 hours, and then cooled to room temperature. After adding 50 ml of water to the reaction solution, the organic layer was recovered, washed with 25 ml of water twice and the solvent was distilled off under reduced pressure to give 7.13 g of crude product. The crude product proved to contain 76.3% of the objective isopropyl (E)-α-methoxyimino-2-(bromomethyl) phenylacetate, 4.8% of the starting material and 13.5% of isopropyl (E)-α-methoxyimino-2-(dibromomethyl) phenylacetate (hereinafter, "iPr-dibromo compound") by gas chromatography analysis.

To 6.53 g of the crude product, 25.00 g of n-hexane was added and the mixture was heated to 73–75° C. to form a homogeneous solution. The solution was cooled to 3 to 5° C. over 3.5 hours and kept at the same temperature for one hour to age precipitated crystals. The crystals were filtered off in vacuo, washed with 10.00 g of cool n-hexane twice and dried to give 4.00 g of isopropyl (E)-α-methoxyimino-2-(bromomethyl)phenylacetate. This purified product proved to contain 96.4% of the objective product, 0.9% of the starting material and 3.2% of iPr-dibromo compound by gas chromatography analysis. mp 76.0–77.0° C.

$^1$H-NMR(CDCl$_3$/TMS,300 MHz, δ (ppm)) 1.30(6H,d,J=5 Hz), 4.04(3H,s), 4.34(2H,s), 5.18(1H,sept,J=5 Hz), 7.14(1H, m), 7.15–7.35(3H,m)

Production Example 3

A mixture of 12.72 g of sodium carbonate pulverized by a centrifugal pulverizer (120 mmol), 10.36 g of methyl (E)-α-methoxyimino-o-tolylacetate (50 mmol) and 29.94 g of chlorobenzene was heated up to 85° C. with vigorous stirring. Under a nitrogen stream, 9.59 g of vaporized bromine gas (60 mmol) was blown into the mixture for 1 hour. After the blowing, the reaction solution was kept at 86 to 88° C. for 2 hours, and then it was cooled to room temperature. After adding 100 ml of water to the reaction solution, the organic layer was recovered, washed with 50 ml of water twice and the solvent was distilled of f under reduced pressure to give 13.21 g of crude product. The crude product proved to contain 79.5% of the objective methyl (E)-α-methoxyimino-2-(bromomethyl)phenylacetate, 5.1% of the starting material and 13.7% of methyl (E)-α-methoxyimino-2-(dibromomethyl)phenylacetate (hereinafter, "Me-dibromo compound") by gas chromatography analysis.

To 6.00 g of the crude product, 25.00 g of n-hexane were added and the mixture was heated to 73–75° C. to form a homogeneous solution. This solution was cooled to 3–5° C. over 3.5 hours, kept at the same temperature for one hour and to try to purify the objective product by recrystallization. However, the crystal of methyl (E)-α-methoxyimino-2-(bromomethyl)phenylacetate was not precipitated.

Production Example 4

The same procedure as the above Production Example 3 was conducted except using 11.76 g of isopropyl (E)-α-methoxyimino-o-tolylacetate (50 mmol) and 9.84 g of sodium acetate (120 mmol) in place of 10.36 g of methyl (E)-α-methoxyimino-o-tolylacetate (50 mmol) and 12.72 g of sodium carbonate (120 mmol) to give 13.96 g of crude product. The crude product proved to contain 78.5% of the objective isopropyl (E)-α-methoxyimino-2-(bromomethyl) phenylacetate, 6.1% of the starting material and 13.0% of iPr-dibromo compound by gas chromatography analysis.

Production Example 5

The same procedure as the above Production Example 3 was conducted except using 11.76 g of isopropyl (E)-α-methoxyimino-o-tolylacetate (50 mmol) and 10.08 g of sodium hydrogencarbonate (120 mmol) in place of 10.36 g of methyl (E)-α-methoxyimino-o-tolylacetate (50 mmol) and 12.72 g of sodium carbonate (120 mmol) to give 12.35 g of crude product. The crude product proved to contain 75.2% of the objective isopropyl (E)-α-methoxyimino-2-(bromomethyl) phenylacetate, 17.2% of the starting material and 6.1% of iPr-dibromo compound by gas chromatography analysis.

Reference Example 1

The same procedure as the above Production Example 1 was conducted except for the omission of sodium carbonate, to give 7.23 g of crude product. The crude product proved to contain 4.8% of the objective product and 84.5% of the starting material by gas chromatography analysis.

Reference Example 2

The same procedure as the above Production Example 2 was conducted except for the omission of sodium carbonate to give 5.65 g of crude product. The crude product proved to contain 25.7% of the objective product and 60.8% of the starting material by gas chromatography analysis.

The production example of the 2-methylphenylacetic acid derivative of the formula (IV) is shown below.

Reference Example 3

(1) To a solution containing 19.2 g of ethyl 2-methylbenzoylformate (0.1 mol) and 100 ml of ethanol, 7.6 g of hydroxylamine hydrochloride (0.11 mol) was added and the resulting mixture was heated under reflux for 5 hours. Afterwards, the solvent was distilled off under reduced pressure as a work-up procedure to give a solid. The solid, to which hexane was added, was pulverized and 14.1 g of ethyl (E)-α-hydroxyimino-o-tolylacetate (yield; 68%) was filtered off. Furthermore, the concentrated residue of the filtrate, to which ethanol and a catalytic amount of thionyl chloride were added, was heated under reflux for 5 hours. The same work-up procedure as shown above was then employed to give 4.5 g of the objective product (yield; 21%). mp 88.0–89.0° C.

$^1$H-NMR(CDCl$_3$/TMS,300 MHz, δ (ppm)) 1.25(3H,t,J=8 Hz), 2.21(3H,s), 4.28(2H,q,J=8 Hz), 7.15(1H,dd,J=8,1 Hz), 7.20–7.40(3H,m), 10.25(1H,brs)

The same procedure as above using an 2-propanol solution of isopropyl 2-methylbenzoylformate (20.6 g, 0.1 mol) gives 14.9 g of isopropyl (E)-α-hydroxyimino-o-tolylacetate (yield; 68%). mp 77.0–78.0° C.

$^1$H-NMR(CDCl$_3$/TMS,300 MHz, δ (ppm)) 1.27(6H,d,J=6 Hz), 2.23(3H,s), 5.16(1H,sept,J=6 Hz), 7.15(1H,dd,J=8.1 Hz), 7.2–7.4(3H,m), 9.78(1H,brs)

(2) To 50 ml of a THF solution with 10.0 g of ethyl (E)-α-hydroxyimino-o-tolylacetate (48 mmol), 2.2 g of 60%-sodium hydride (53 mmol) was added under ice-cooling and the solution was stirred for 30 minutes. The solution, to which 6.7 g of dimethyl sulfate (53 mmol) was added dropwise, was stirred at room temperature for one more hour. Water and ethyl acetate were added to the reaction solution, and the organic layer was washed with water, dried over anhydrous magnesium sulfate and concentrated to give 10.4 g of ethyl (E)-α-methoxyimino-o-tolylacetate (yield; 98%).

$^1$H-NMR(CDCl$_3$/TMS,300 MHz, δ (ppm)) 1.33(3H,t,J=8 Hz), 2.19(3H,s), 4.04(3H,s), 4.33(2H,q,J=8 Hz), 7.12(1H, dd,J=8.1 Hz), 7.15–7.40(3H,m)

The same procedure as above using 10.0 g of isopropyl (E)-α-hydroxyimino-o-tolylacetate (46 mmol) gives 10.1 g of isopropyl (E)-α-methoxyimino-o-tolylacetate (yield 75%).

$^1$H-NMR(CDCl$_3$/TMS,300 MHz, δ (ppm)) 1.28(6H,d,J=6 Hz), 2.19(3H,s), 4.02(3H,s), 5.17(1H,sept,J=6 Hz), 7.09(1H, dd,J=8.1 Hz), 7.15–7.35(3H,m)

The production examples of dithiocarbonimide compounds described in U.S. Pat. No. 5,563,159 using the benzyl bromide derivatives obtained in the present invention are shown below.

Reference Example 4

(1) A mixture of 6.0 g of ethyl (E)-α-methoxyimino-2-(bromomethyl)phenylacetate (content;95.8%, 19 mmol), 4.05 g of methyl 4-ethylphenyldithiocarbamate (19 mmol), 0.33 g of tetra-n-butylammonium bromide (1 mmol) and 20 ml of toluene was stirred vigorously, and 2.50 ml of 8M aqueous solution of sodium hydroxide (20 mmol) was added dropwise to the mixture while keeping the temperature of the mixture under 10° C. After dropping, the reaction mixture was stirred at 20° C. for 2 more hours. To the mixture, 20 ml of water was added and the organic layer was recovered and dried over anhydrous magnesium sulfate. After anhydrous magnesium sulfate was filtered off, the solvent was distilled off under reduced pressure to give an oily product. A small amount of ethanol was added to the oily product. The oily product was solidified under ice-cooling, pulverized and filtered to give 6.63 g of S-[2-((E)-α-methoxyimino-α-ethoxycarbonyl)methyl]phenylmethyl-S-methyl-N-(4-ethylphenyl)dithiocarbonimide (yield; 81%).

mp 69.0–70.0° C. $^1$H-NMR(CDCl$_3$/TMS,300 MHz, ((ppm)) 1.21(3H,t,J=6 Hz), 1.28(3H,t,J=6 Hz), 2.42(3H,s), 2.61(2H,q,J=6 Hz), 4.02(3H,s), 4.21(2H,s), 4.25(2H,q,J=6 Hz), 6.78(2H,d,J=8 Hz), 7.0–7.6(6H,m)

(2) To a dilution of 5.0 g of S-[2-((E)-α-methoxyimino-α-ethoxycarbonyl)methyl]phenylmethyl-S-methyl-N-(4-ethylphenyl)dithiocarbonimide (12 mmol) in 25 ml of ethanol, 4.65 g of a 40% methylamine aqueous solution (60 mmol) was added and the mixture was stirred at room temperature for 7 hours. After the completion of the reaction, water was added to the mixture. Methylamine and ethanol were distilled off under reduced pressure to give a residue, to which toluene was added. The recovered organic layer was dried over anhydrous magnesium sulfate. The solvent was distilled off under reduced pressure to give a solid product. The solid product, to which diisopropyl ether was added, was pulverized and filtered to give 4.58 g of S-{2-[(E)-α-methoxyimino-α-(N-methylcarbamoyl)]methyl} phenylmethyl-S-methyl-N-(4-ethylphenyl) dithiocarbonimide (yield; 92%).

Reference Example 5

(1) A mixture of 5.0 g of isopropyl (E)-α-methoxyimino-2-(bromomethyl)phenylacetate (content;96.4%, 15 mmol), 3.25 g of methyl 4-ethylphenyldithiocarbamate (15 mmol), 4.20 g of anhydrous potassium carbonate and 25 ml of 2-propanol was stirred at 50° C. for 4 hours. Insoluble materials were filtered off through celite and washed with 2-propanol. The filtrate was distilled off under reduced pressure to give an oily product. Toluene and water were added to the oily product. The recovered organic layer was washed with water and dried over anhydrous magnesium sulfate. After anhydrous magnesium sulfate was filtered off, the solvent was distilled off under reduced pressure to give an oily product. Ethanol was added to the oily product. The oily product was solidified under ice-cooling, pulverized and filtered to give 5.53 g of S-[2-((E)-α-methoxyimino-α-isopropoxycarbonyl)methyl]phenylmethyl-S-methyl-N-(4-ethylphenyl)dithiocarbonimide (yield; 87%). mp 85.0–86.0° C.

$^1$H-NMR(CDCl$_3$/TMS,300 MHz, δ (ppm)) 1.21(3H,t,J=6 Hz), 1.25(6H,d,J=6 Hz), 2.42(3H,s), 2.61(2H,q,J=6 Hz), 4.02(3H,s), 4.22(2H,s), 5.12(1H,sept,J=6 Hz), 6.79(2H,d, J=8 Hz), 7.0–7.6(6H,m)

(2) To a dilution of 5.0 g of S-[2-((E)-α-methoxyimino-α-isopropoxycarbonyl)methyl]phenylmethyl-S-methyl-N-(4-ethylphenyl)dithiocarbonimide (11 mmol) in 20 ml of ethanol and 5 ml of chlorobenzene, 4.26 g of 40% methylamine aqueous solution (55 mmol) was added and the mixture was stirred at room temperature overnight. After the completion of the reaction, water was added to the mixture. Methylamine and the solvents were distilled off under reduced pressure to give a residue, to which toluene was added. The recovered organic layer was dried over anhydrous magnesium sulfate. The solvent was distilled off under reduced pressure to give an oily product. The oily product was purified by silica gel column chromatography to give 1.40 g of the starting material (yield; 28%) and 2.96 g of S-{2-[(E)-α-methoxyimino-α-(N-methylcarbamoyl)]methyl}phenylmethyl-S-methyl-N-(4-ethylphenyl) dithiocarbonimide (yield; 65%).

What is claimed is:

1. A method for producing a benzyl bromide derivative of the formula:

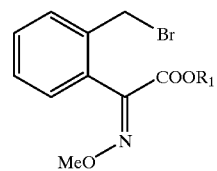

(wherein R$_1$ represents a C$_1$ to C$_5$ alkyl group) which comprises reacting a 2-methylphenylacetic acid derivative of the formula:

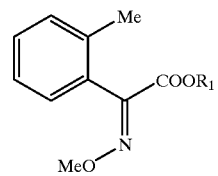

(wherein R$_1$ means the same as above) with bromine in the presence of an alkali metal salt.

2. The method according to claim 1, wherein the alkali metal salt is at least one selected from carbonate, phosphate and carboxylate.

3. A method for producing a benzyl bromide derivative of the formula:

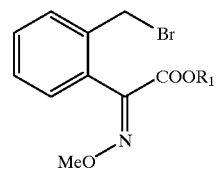

(wherein R$_1$ represents an ethyl or isopropyl group) which comprises reacting a 2-methylphenylacetic acid derivative of the formula:

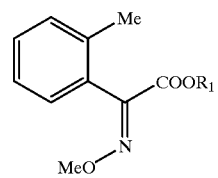

(wherein R$_1$ means the same as above) with bromine in the presence of an alkali metal salt and then recrystallizing the reaction product from aliphatic hydrocarbon solution.

4. The method according to claim 3, wherein the alkali metal salt is at least one selected from carbonate, phosphate and carboxylate.

5. The method according to claim 3, wherein the aliphatic hydrocarbon is at least one selected from n-hexane, n-heptane and n-octane.

6. The method according to claim 3, wherein the alkali metal salt is at least one selected from carbonate, phosphate and carboxylate; and the aliphatic hydrocarbon is at least one selected from n-hexane, n-heptane and n-octane.

* * * * *